United States Patent
Robins (10) Patent No.: US 12,195,795 B2
(45) Date of Patent: *Jan. 14, 2025

(54) SYNTHETIC STRANDS FOR NUCLEIC ACID SEQUENCING AND RELATED METHODS AND SYSTEMS

(71) Applicant: Adaptive Biotechnologies Corporation, Seattle, WA (US)

(72) Inventor: Harlan S. Robins, Seattle, WA (US)

(73) Assignee: Adaptive Biotechnologies Corporation, Seattle, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/224,496

(22) Filed: Jul. 20, 2023

(65) Prior Publication Data

US 2024/0052411 A1 Feb. 15, 2024

Related U.S. Application Data

(63) Continuation of application No. 17/090,818, filed on Nov. 5, 2020, now Pat. No. 11,708,605.
(Continued)

(51) Int. Cl.
| | |
|---|---|
| *C12Q 1/68* | (2018.01) |
| *C12Q 1/6869* | (2018.01) |
| *G16B 30/00* | (2019.01) |

(52) U.S. Cl.
CPC ........... *C12Q 1/6869* (2013.01); *G16B 30/00* (2019.02)

(58) Field of Classification Search
CPC .............................. C12Q 1/6869; G16B 30/00
See application file for complete search history.

(56) References Cited

U.S. PATENT DOCUMENTS 11,708,605 B2 * 7/2023 Robins ............... G16B 30/00
435/6.11
2005/0124010 A1   6/2005 Short et al.
(Continued)

FOREIGN PATENT DOCUMENTS

WO   2000022171   4/2000

OTHER PUBLICATIONS

Brown et al., (1990) "Influence of pH on the conformation and stability of mismatch base-pairs in DNA", J. Mol. Biol., vol. 212, No. 3, pp. 437-440.
(Continued)

*Primary Examiner* — Jezia Riley
(74) *Attorney, Agent, or Firm* — Brian E. Davy; Bozicevic, Field & Francis LLP (57) ABSTRACT

Provided are synthetic strands for nucleic acid sequencing. In some embodiments, the strands include a plurality of rotatable solid supports. The plurality of rotatable solid supports comprises solid supports each comprising on its surface a first moiety that binds to adenine (A), a second moiety that binds to cytosine (C), a third moiety that binds to guanine (G), a fourth moiety that binds to thymine (T), uracil (U), or both (T/U). Each of such solid supports further comprises on its surface a position marker that indicates the rotational position of the solid support, where the first, second, third, and fourth moieties are spaced about the circumference of the solid support. The solid supports enable hybridization of the synthetic strand to a nucleic acid. Also provided are methods of using the synthetic strands, as well as related compositions, kits, and nucleic acid sequencing systems.

20 Claims, 2 Drawing Sheets

Related U.S. Application Data

(60) Provisional application No. 63/076,526, filed on Sep. 10, 2020, provisional application No. 62/931,620, filed on Nov. 6, 2019.

(56) References Cited

U.S. PATENT DOCUMENTS

| | | |
|---|---|---|
| 2017/0204152 A1 | 7/2017 | Nelson et al. |
| 2017/0292149 A1 | 10/2017 | SHerwood et al. |
| 2018/0142289 A1 | 5/2018 | Zeitoun et al. |
| 2019/0203275 A1 | 7/2019 | Frisen et al. |

OTHER PUBLICATIONS

Ageno et al., (1969) "The alkaline denaturation of DNA", Biophysical Journal, vol. 9, pp. 1281-1311.

Wilson & Szostak, (1999) "In vitro selection of functional nucleic acids", Annu Rev Biochem. vol. 68, pp. 611-647.

* cited by examiner

FIG. 1

SYNTHETIC STRANDS FOR NUCLEIC ACID SEQUENCING AND RELATED METHODS AND SYSTEMS

CROSS-REFERENCE TO RELATED APPLICATIONS

This application is a continuation of U.S. patent application Ser. No. 17/090,818, filed Nov. 5, 2020, and claims the benefit of U.S. Provisional Patent Application No. 63/076,526, filed Sep. 10, 2020, and U.S. Provisional Patent Application No. 62/931,620, filed Nov. 6, 2019, which applications are incorporated herein by reference in their entireties.

INTRODUCTION

Next-generation sequencing platforms use different technologies for sequencing, such as pyrosequencing, sequencing by synthesis, sequencing by ligation, or nanopore-based sequencing. Most platforms, however, adhere to a common library preparation procedure, with minor modifications, before a 'run' on the instrument. This procedure may include fragmenting the nucleic acids to be sequenced (e.g., by sonication, nebulization or shearing), followed by nucleic acid repair and end polishing (e.g., blunt end or A overhang) and, finally, platform-specific adaptor ligation. This process typically results in considerable sample loss with limited throughput. Roche, Illumina and Life Technologies, among others, have developed well-established platforms for deep sequencing. Regardless of the instrument, one of the bottlenecks for next-generation sequencing is the amount of time and resources required for template and library preparation.

SUMMARY

Provided are synthetic strands for nucleic acid sequencing. In some embodiments, the strands include a plurality of rotatable solid supports. The plurality of rotatable solid supports comprises solid supports each comprising on its surface a first moiety that binds to adenine (A), a second moiety that binds to cytosine (C), a third moiety that binds to guanine (G), a fourth moiety that binds to thymine (T), uracil (U), or both (T/U). Each of such solid supports further comprises on its surface a position marker that indicates the rotational position of the solid support, where the first, second, third, and fourth moieties are spaced about the circumference of the solid support. The solid supports enable hybridization of the synthetic strand to a nucleic acid. Also provided are methods of using the synthetic strands, as well as related compositions, kits, and nucleic acid sequencing systems.

DETAILED DESCRIPTION

Before the synthetic strands, methods and compositions of the present disclosure are described in greater detail, it is to be understood that the synthetic strands, methods and compositions are not limited to particular embodiments described, as such may, of course, vary. It is also to be understood that the terminology used herein is for the purpose of describing particular embodiments only, and is not intended to be limiting, since the scope of the synthetic strands, methods and compositions will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the synthetic strands, methods and compositions. The upper and lower limits of these smaller ranges may independently be included in the smaller ranges and are also encompassed within the synthetic strands, methods and compositions, subject to any specifically excluded limit in the stated range. Where the stated range includes one or both of the limits, ranges excluding either or both of those included limits are also included in the synthetic strands, methods and compositions.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the synthetic strands, methods and compositions belong. Although any synthetic strands, methods and compositions similar or equivalent to those described herein can also be used in the practice or testing of the synthetic strands, methods and compositions, representative illustrative synthetic strands, methods and compositions are now described.

All publications and patents cited in this specification are herein incorporated by reference as if each individual publication or patent were specifically and individually indicated to be incorporated by reference and are incorporated herein by reference to disclose and describe the materials and/or methods in connection with which the publications are cited. The citation of any publication is for its disclosure prior to the filing date and should not be construed as an admission that the present synthetic strands, methods and compositions are not entitled to antedate such publication, as the date of publication provided may be different from the actual publication date which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the synthetic strands, methods and compositions, which are, for clarity, described in the context of separate embodiments, may also be provided in combination in a single embodiment. Conversely, various features of the synthetic strands, methods and compositions, which are, for brevity, described in the context of a single embodiment, may also be provided separately or in any suitable sub-combination. All combinations of the embodiments are specifically embraced by the present disclosure and are disclosed herein just as if each and every combination was individually and explicitly disclosed, to the extent that such combinations embrace operable processes and/or compositions. In addition, all sub-combinations listed in the embodiments describing such variables are also specifically embraced by the present synthetic strands, methods and compositions and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order that is logically possible.

Synthetic Strands for Nucleic Acid Sequencing

The present disclosure provides synthetic strands for nucleic acid sequencing. As will be appreciated upon review of the present disclosure, the synthetic strands and methods of using same for nucleic acid sequencing constitute an improvement over existing sequencing technologies because, e.g., the synthetic strands and sequencing methods of the present disclosure obviate the need for nucleic acid fragmentation, nucleic acid repair and end polishing, and platform-specific adaptor ligation. As a consequence, nucleic acid sequencing using the synthetic strands of the present disclosure may be performed in significantly less time as compared to existing next-generation sequencing technologies.

In certain embodiments, the synthetic strands include a plurality of rotatable solid supports disposed along one or more base strands. The base strand may comprise any biocompatible material. In one preferred embodiment, the base strand is flexible in construction, such as a polymer thread, a flexible elongate nanostructure (e.g., a carbon nanotube), or the like. Alternatively or additionally, the base strand may comprise a cylinder into which the solid supports are disposed.

According to some embodiments, the one or more base strands comprise one or more carbon nanotubes (CNTs). CNTs are cylindrical large molecules consisting of a hexagonal arrangement of hybridized carbon atoms, which may by formed by rolling up a single sheet of graphene (single-walled carbon nanotubes, SWCNTs) or by rolling up multiple sheets of graphene (multiwalled carbon nanotubes, MWCNTs). In certain embodiments, the one or more base strands comprise one or more SWCNTs. According to some embodiments, the one or more base strands comprise one or more MWCNTs. Methods for making CNTs are known and include arc discharge, laser ablation of graphite, and chemical vapor deposition (CVD). In arc discharge and laser ablation of graphite, graphite is combusted electrically or by means of a laser, and the CNTs developing in the gaseous phase are separated. In the CVD process, a metal catalyst (such as iron) may be combined with carbon-containing reaction gases (such as hydrogen or carbon monoxide) to form carbon nanotubes on the catalyst inside a high-temperature furnace. The CVD process can be purely catalytic or plasma-supported. The plasma-supported approach requires slightly lower temperatures (200-500° C.) than the catalytic process (up to 750° C.) and aims at producing 'lawn-like' CNT growth. Once produced, carbon nanotubes may be purified using known methods such as acid treatment, ultrasound, or the like.

In certain embodiments, the one or more base strands comprise one or more carbon nanofibers (CNFs). CNFs do not have the same lattice structure as CNTs. Instead, they consist of a combination of several forms of carbon and/or several layers of graphite, which are stacked at various angles on amorphous carbon (where atoms do not arrange themselves in ordered structures). CNFs have similar properties as CNTs, but their tensile strength is lower owing to their variable structure, and they are not hollow on the inside.

The plurality of rotatable solid supports comprises solid supports each comprising on its surface a first moiety that binds to adenine (A), a second moiety that binds to cytosine (C), a third moiety that binds to guanine (G), a fourth moiety that binds to thymine (T), uracil (U), or both (T/U). The plurality of rotatable solid supports comprises solid supports each further comprising on its surface a position marker that indicates the rotational position of the solid support, where the first, second, third, and fourth moieties are spaced about the circumference of the solid support. The solid supports are sized and spaced along the base strand to enable hybridization of the synthetic strand to a nucleic acid.

In a preferred embodiment described further herein, the solid supports are rotatable independently of one another. In such embodiments, the supports may be secured along one or more base strands threaded through a bore in each support. The relative position of each support along the base strand may be secured by restricting its movement along the strand; e.g., by tying off or thickening the strand(s) between solid supports or otherwise treating the base strand(s) to restrict such movement by chemically repulsing the solid supports from moving closer together along the vertical axis of the strand. The solid supports may also be disposed along a base strand at discrete points. One or more supports may also be rotatably linked to one another. In addition, one or more of the solid supports (disposed along an internally threaded base strand or not) may be disposed longitudinally within a cylindrical structure (e.g., a biocompatible tube).

The synthetic strands of the present disclosure enable a new approach to nucleic acid sequencing. Current nucleic acid sequencing technologies suffer from a number of drawbacks including insufficient speed, e.g., for point of care clinical use. This is because such technologies sequence by adding one base at a time, reading out a signal, and then moving to the next base.

The synthetic strands of the present disclosure enable a new approach to nucleic acid sequencing that addresses the drawbacks of the current technologies. The solid supports are sized and spaced to enable hybridization of the synthetic strand to a nucleic acid. When the synthetic strand comes into contact with a nucleic acid (DNA, RNA, cDNA, or the like), the solid supports rotate such that one of the first, second, third or fourth moieties binds (e.g., by hydrogen bonding) to the nucleobase of the nucleotide at the corresponding position of the nucleic acid. The position marker indicates the rotational position of the solid support and, in turn, indicates the identity of the nucleotide (an A-, C-, G- or T/U-containing nucleotide) to which the solid support is bound.

As such, determining the sequence of the nucleic acid involves determining the sequential positions of the position markers of the synthetic strand as determined by the nucleotide sequence of the nucleic acid. To that end, systems and kits including position marker readers and reagents are also provided. This sequencing approach may be performed much more rapidly than existing technologies and obviates the need for polymerases, sequencing by synthesis, and the like. Details regarding embodiments of the synthetic strands will now be described.

The synthetic strands comprise a plurality of rotatable solid supports. The term "solid support" means an insoluble material having a surface to which reagents or materials can be attached, e.g., allowing them to be readily separated from a solution. The solid supports of the present disclosure are particulate in nature. According to some embodiments, the solid supports have an average greatest linear dimension of from 0.1 nm to 100 nm. For example, in certain embodiments, the solid supports have an average greatest linear dimension of greater than 0.3 nm and less than 80 nm, less than 70 nm, less than 60 nm, less than 50 nm, less than 40 nm, less than 30 nm, less than 20 nm, less than 10 nm, less than 5 nm, less than 4 nm, less than 3 nm, less than 2 nm, or less than 1 nm. According to some embodiments, the solid supports have an average greatest linear dimension of from 0.5 to 10 nm, e.g., from 0.5 to 5 nm. When the solid supports are spherical or substantially spherical/spheroid (e.g., beads), the average greatest linear dimension is the average diameter of the solid supports.

The rotatable solid supports may be made of a variety of materials. Support materials include any material that can act as a support for attachment of the moieties, position marker(s), and any other desired features. Suitable materials include, but are not limited to, organic or inorganic polymers, natural and synthetic polymers, including, but not limited to, agarose, cellulose, nitrocellulose, cellulose acetate, other cellulose derivatives, dextran, dextran-derivatives and dextran co-polymers, other polysaccharides, glass, silica gels, gelatin, polyvinyl pyrrolidone, rayon, nylon, polyethylene, polypropylene, polybutylene, polycarbonate, polyesters, polyamides, vinyl polymers, polyvinylalcohols, polystyrene and polystyrene copolymers, polystyrene cross-linked with divinylbenzene or the like, acrylic resins, acrylates and acrylic acids, acrylamides, polyacrylamides, polyacrylamide blends, co-polymers of vinyl and acrylamide, methacrylates, methacrylate derivatives and co-polymers, other polymers and co-polymers with various functional groups, latex, butyl rubber and other synthetic rubbers, silicon, glass, paper, natural sponges, insoluble protein, surfactants, metals, metalloids, magnetic materials, and any combinations thereof.

The rotatable solid supports may be any suitable shape, including but not limited to spherical, spheroid, cube-shaped, cuboidal, rod-shaped, disk-shaped, pyramid-shaped, cylinder-shaped, nanohelical-shaped, nanospring-shaped, nanoring-shaped, arrow-shaped, teardrop-shaped, tetrapod-shaped, prism-shaped, or any other suitable geometric or non-geometric shape. In certain embodiments, the rotatable solid supports are non-spherical, where each solid support has five faces—one face for each moiety and a face for the position marker. According to some embodiments, the rotatable solid supports are non-spherical, where each solid support has seven faces—one face for each moiety, a face for the position marker, a face for attaching a first linker, and a face for attaching a second linker.

In certain embodiments, the solid supports are beads. As used herein, the term "bead" refers to a small mass that is generally spherical or spheroid in shape. According to some embodiments, a bead as used herein has an average diameter of from about 0.5 to 10 nm, e.g., from 0.5 to 5 nm.

Additionally, and for purposes herein, the solid supports may be magnetically responsive, e.g., by virtue of comprising one or more paramagnetic and/or superparamagnetic substances, such as for example, magnetite. Such paramagnetic and/or superparamagnetic substances may be embedded within the matrix of the solid supports, and/or may be disposed on an external and/or internal surface of the solid support.

The solid supports of a synthetic strand of the present disclosure are rotatable. By "rotatable" is meant a solid support, when disposed along a base strand between first and second neighboring solid supports, can readily rotate about its circumference such that the first, second, third or fourth moiety may be positioned for binding to a nucleobase of the corresponding nucleotide of a nucleic acid. In one embodiment, each solid support includes a bore through its body into which a base strand is disposed (e.g., forming a string of "beads"). In such embodiments, a solid support rotates around both its own circumference and that of the base strand. Alternatively, or additionally, the base strand may comprise a cylindrical structure in which the solid supports are longitudinally disposed. Each solid support is preferably separately disposed on or in the synthetic base strand to allow for its rotation independent of other solid supports on the base, although one or more supports may optionally be linked (rotatably or otherwise) to one another as well.

Approaches for providing the solid supports along the one or more base strands (e.g., one or more carbon nanotubes, one or more carbon nanofibers, or the like) include, but are not limited to, combining the solid supports and the one or more base strands in a mixture and allowing the synthetic strand to assemble. For example, each solid support may include a bore through its body through which the one or more base strands (e.g., CNT, CNF, or the like) thread upon combining the solid supports and the one or more base strands in a mixture. The components may be combined at a suitable temperature (e.g., 30° C.-50° C., such as 37° C.) and pH (e.g., pH 7-pH 8.5) to permit assembly of the synthetic strands.

A variety of linkers may be employed in the synthetic strand to permit linking of components of the strand as desired, and/or linking the strand to a substrate, such as a microplate or flow cell. According to some embodiments, the linkages are formed with flexible polymeric linkers comprising natural or non-natural polymers. Non-limiting examples include peptides, lipid oligomers, liposaccharide oligomers, peptide nucleic acid oligomers, polylactate, polyethylene glycol (PEG), cyclodextrin, polymethacrylate, gelatin, and oligourea.

In some embodiments, flexible peptide linkers are employed. For example, suitable linkers include those comprising glycine and serine (glycine-serine linkers), where the flexibility of such linkers may be tuned based on the inverse relationship between linker stiffness and glycine content. According to some embodiments, two or more components of the strand are linked via flexible poly(ethylene glycol) (or "PEG") linkers. Purified PEG is available commercially as mixtures of different oligomer sizes in broadly or narrowly defined molecular weight (MW) ranges. For example, "PEG 600" typically denotes a preparation that includes a mixture of oligomers having an average MW of 600. Likewise, "PEG 10000" denotes a mixture of PEG molecules (n=195 to 265) having an average MW of 10,000 g/mol.

A variety of suitable approaches are available for such attachment use of linkers. For example, the surface of a solid support may be functionalized (or "activated"/"derivatized") with reactive groups to which the linkers (and optionally, the first, second, third, and fourth moieties, the position marker, and/or any combination thereof), may bind to become directly bound to the surface of the solid support. The surface of the solid support may be functionalized with any useful/convenient reactive group, including but not limited to thiol groups (—SH), amine groups (—NH2), carboxyl groups (—COO), and/or the like.

Any desirable component of the rotatable solid supports (e.g., the surface thereof, a linker, the first, second, third, and fourth moieties, the position marker, and/or any combination thereof) may be bound to a second desirable component, e.g., by reacting a first portion of a linker molecule with a first portion of one of the components, and subsequently reacting a second portion of the linker molecule a second component. Suitable strategies include those described in Chemistry of Bioconjugates: Synthesis, Characterization, and Biomedical Applications (Narain, Ed.) ISBN-10: 9781118359143; Bioconjugate Techniques (Hermanson) ISBN-10: 0123822394; and the surface modification/functionalization literature.

Functional groups that may be used to bind components of the synthetic base strands/solid supports include, but are not limited to, active esters, isocyanates, imidoesters, hydrazides, amino groups, aldehydes, ketones, photoreactive groups, maleimide groups, alpha-halo-acetyl groups, epoxides, azridines, and the like. Reagents such as iodoacetamides, maleimides, benzylic halides and bromomethylketones react by S-alkylation of thiols to generate stable thioether products. For example, at pH 6.5-7.5, maleimide groups react with sulfhydryl groups to form stable thioether bonds. Arylating reagents such as NBD halides react with thiols or amines by a similar substitution of the aromatic halide by the nucleophile. Because the thiolate anion is a better nucleophile than the neutral thiol, cysteine is more reactive above its $pK_a$ (~8.3, depending on protein structural context). Thiols also react with certain amine-reactive reagents, including isothiocyanates and succinimidyl esters. The TS-Link series of reagents are available for reversible thiol modification.

With respect to amine reactive groups, primary amines exist at the N-terminus of polypeptide chains and in the side-chain of lysine (Lys, K) amino acid residues. Among the available functional groups in proteins (e.g., peptide linkers, etc.), primary amines are especially nucleophilic, making them ready targets for conjugation with several reactive groups. For example, NHS esters are reactive groups formed by carbodiimide-activation of carboxylate molecules. NHS ester-activated crosslinkers and labeling compounds react with primary amines in physiologic to slightly alkaline conditions (pH 7.2 to 9) to yield stable amide bonds. The reaction releases N-hydroxysuccinimide (NHS). Also by way of example, imidoester crosslinkers react with primary amines to form amidine bonds. Imidoester crosslinkers react rapidly with amines at alkaline pH but have short half-lives. As the pH becomes more alkaline, the half-life and reactivity with amines increases. As such, crosslinking is more efficient when performed at pH 10 than at pH 8. Reaction conditions below pH 10 may result in side reactions, although amidine formation is favored between pH 8-10.

Numerous other synthetic chemical groups will form chemical bonds with primary amines, including but not limited to, isothiocyanates, isocyanates, acyl azides, sulfonyl chlorides, aldehydes, glyoxals, epoxides, oxiranes, carbonates, aryl halides, carbodiimides, anhydrides, and fluorophenyl esters. Such groups conjugate to amines by either acylation or alkylation.

The plurality of rotatable solid supports comprises solid supports each comprising on its surface a first moiety that binds to adenine (A), a second moiety that binds to cytosine (C), a third moiety that binds to guanine (G), and a fourth moiety that binds to thymine (T), uracil (U), or both (T/U). Any moieties capable of preferential or specific binding to A, C, G, or T/U may be employed. In certain embodiments, the moieties comprise natural nucleobases, where the first moiety comprises T or U for binding to A, the second moiety comprises G for binding to C, the third moiety comprises C for binding to G, and the fourth moiety comprises A for binding to T/U. The term "nucleobase" refers to a nitrogen-containing heterocyclic moiety, which are the parts of natural nucleic acids that are involved in the hydrogen-bonding and bind one nucleic acid strand to another complementary strand in a sequence specific manner. The most common naturally-occurring nucleobases are: adenine (A), cyctosine (C), guanine (G), thymine (T), and uracil (U).

According to some embodiments, the moieties comprise non-natural nucleobases. The term "non-natural nucleobase" refers to a non-natural nucleobase moiety that mimics the spatial arrangement, electronic properties, and/or some other physiochemical property of a natural nucleobase and retains the property of the hydrogen bonding that binds one nucleic acid strand to another in a sequence specific manner. A modified nucleobase can pair with at least one of the five naturally-occurring bases (uracil, thymine, adenine, cytosine, and guanine).

In certain embodiments, the moieties comprise a "non-natural nucleoside" or "non-natural nucleotide", which refer to a nucleoside or nucleotide that contains a modified nucleobase and/or other chemical modification, such as a modified sugar. According to some embodiments, the solid supports comprise moieties that comprise non-natural nucleobases and/or non-natural nucleotides that modify the melting temperature ($T_m$) of a synthetic strand-nucleic acid hybrid as compared to a nucleic acid-nucleic acid hybrid. Non-limiting examples include modified pyrimidine such as methyl-dC or propynyl-dU; modified purine, e.g., G-clamp; 2-Amino-2'-deoxyadenosine-S-Triphosphate (2-Amino-dATP), 5-Methyl-2'-deoxycytidine-5'-Triphosphate (5-Me-dCTP), 5-Propynyl-2'-deoxycytidine-5'-Triphosphate (5-Pr-dCTP), 5-Propynyl-2'-deoxyuridine-5'-Triphosphate (5-Pr-dUTP), a halogenated deoxyuridine (XdU) such as 5-Chloro-2'-deoxyuridine-5'-Triphosphate (5-CI-dUTP), 5-Bromo-2'-deoxyuridine-5'-Triphosphate (5-Br-dUTP), or any combination thereof.

The plurality of rotatable solid supports comprises solid supports each comprising on its surface a position marker. In certain embodiments, each solid support comprises a single position marker. According to some embodiments, each solid support comprises 2 or more position markers, e.g., 2 or more, 3 or more, 4 or more, or 5 or more position markers. As used herein, a "position marker" is a component of the solid support that indicates the rotational position of the solid support with respect to the first, second, third and fourth moieties—that is, when the synthetic strand becomes hybridized to a nucleic acid in a test sample, the position marker indicates which of the first, second, third or fourth moieties are bonded (e.g., hydrogen-bonded) to a nucleobase of the nucleic acid.

A variety of types of the position markers may be employed. According to some embodiments, the position markers of the plurality of rotatable solid supports are independently selected from a fluorophore, a quencher, a magnetic molecule, and a metal. As such, in certain embodiments, one or more of the positions markers are fluorophores. The term "fluorophore" refers to a substance or a portion thereof which is capable of exhibiting fluorescence in the detectable range. Non-limiting examples of fluorophores which may be used as position markers include fluorescein and its derivatives (e.g., fluorescein isothiocyanate (FITC)); rhodamine and its derivatives; cyanine and its derivatives; coumarin and its derivatives; Cascade Blue and its derivatives; Lucifer Yellow and its derivatives; BODIPY and its derivatives; and the like. Fluorophores of interest also include phycoerythrin (PE), R-phycoerythrin (R-PE), indocarbocyanine (C3), indodicarbocyanine (C5), Cy3, Cy3.5, Cy5, Cy5.5, Cy7, Texas Red, Pacific Blue, Oregon Green 488, Alexa fluor-355, Alexa Fluor 488, Alexa Fluor 532, Alexa Fluor 546, Alexa Fluor-555, Alexa Fluor 568, Alexa Fluor 594, Alexa Fluor 647, Alexa Fluor 660, Alexa Fluor 680, Alexa Fluor 700, JOE, Lissamine, Rhodamine Green, BODIPY, fluorescein isothiocyanate (FITC), carboxy-fluorescein (FAM), phycoerythrin, rhodamine, dichlororhodamine (dRhodamine), carboxy tetramethylrhodamine (TAMRA), carboxy-X-rhodamine (ROX), LIZ, VIC, NED, PET, SYBR, PicoGreen, RiboGreen, and the like.

According to some embodiments, the position markers of the plurality of rotatable solid supports comprise fluorophore-quencher pairs. For example, the relative rotational positions of two neighboring solid supports may be indicated by the presence or absence of quenching of fluorophores on the solid supports. The fluorophore-quencher pairs are selected such that they are compatible with one another. For example, when one or more quenchers are employed, the fluorophore and the one or more quenchers are selected such that the one or more quenchers are capable of absorbing energy from the fluorophore (e.g., a fluorescent dye) and re-emitting much of that energy as either non-radiative energy (in the case of a dark quencher) or visible light (in the case of a fluorescent quencher). When the fluorophore and the one or more quenchers are in close proximity, the one or more quenchers absorb the energy emitted from the excited fluorophore, thereby suppressing its emission. When the one or more quenchers are widely separated from the fluorophore, the one or more quenchers no longer can absorb the fluorophore's emission, and the fluorophore can be visually detected. Examples of quenchers that can be used include TAM RA, Dabcyl, Eclipse® Dark Quencher, BHQ series, and DDQ series. Examples of possible combinations of the fluorophore and the quencher include, but are not limited to, combinations of ALEXA 350 with BHQ-0, FAM with BHQ-1, ROX with BHQ-2, Cy5 with BHQ-3, TET with Dabcyl, Fluorescein with TAMRA, HEX with DDQ I, Rhodamine 6G with DDQ II, and Yakima Yellow with Eclipse® Dark Quencher.

The solid supports of the synthetic strands of the present disclosure are sized and spaced along a base strand to enable hybridization of the synthetic strand to a nucleic acid. With the benefit of the present disclosure coupled with the known dimensions and spacing of nucleotides, nucleobases, etc. in natural nucleic acids, one of ordinary skill can select a suitable combination of solid support size and separation between solid supports to permit hybridization of the synthetic strand to a nucleic acid. In certain embodiments, the solid supports are sized and spaced to enable hybridization of the synthetic strand to a nucleic acid in a double-helical conformation.

According to some embodiments, a synthetic strand of the present disclosure further comprises a series of solid supports spaced along a base strand, each solid support of the series comprising on its surface a moiety for binding to A, C, G, or T/U, wherein each solid support of the series binds exclusively to A, C, G, or T/U, and wherein the series is designed to hybridize to a known nucleic acid sequence. Known sequences of interest include genomic DNA sequences, cDNA sequence, RNA sequences (e.g., mRNA sequences), adapter sequences, and the like. In certain embodiments, the known sequence is an adapter sequence. For example, an adapter sequence (e.g., oligonucleotide of known nucleotide sequence) may be added to nucleic acids of a nucleic acid sample (e.g., by ligation, PCR, or any other suitable adapter addition strategy), where the series of solid supports is designed to be complementary (and hybridize) to the adapter sequence. This provides a binding site for the synthetic strands on the adapted nucleic acids for subsequent determination of the sequence of a non-adapter portion of the adapted nucleic acids based on the rotational positions of the plurality of solid supports indicated by the position markers.

According to some embodiments, the series of solid supports which exclusively bind to A, C, G, or T/U is designed to be complementary (and hybridize) to a known sequence of a non-adapted nucleic acid (or a known sequence of a non-adapted portion of an adapted nucleic acid). Such embodiments find use, e.g., when it is desirable to use the synthetic strands for targeted sequencing of a portion of a nucleic acid of interest, where the series of solid supports which exclusively bind to A, C, G, or T/U is designed to be complementary (and hybridize) to a region adjacent to that portion of the nucleic acid of interest. In certain embodiments, the known sequence of the nucleic acid of interest to which the series of solid supports may be designed to bind include is a genomic DNA sequence. According to some embodiments, the series of solid supports is designed to bind to a region adjacent a region that encodes a variable domain of a T cell receptor (TCR) (e.g., a region adjacent a region that encodes the CDR3 of a TCR) or a B cell receptor (e.g., a region adjacent a region that encodes a variable domain of an antibody).

In certain embodiments, the series of solid supports which exclusively bind to A, C, G, or T/U is designed to be complementary (and hybridize) to a homopolymeric sequence of a non-adapted nucleic acid (or a homopolymeric sequence of a non-adapted portion of an adapted nucleic acid). In some embodiments, the series of solid supports is designed to bind to a polyA sequence. Such embodiments find use, e.g., when it is desirable to use the synthetic strands to sequence poly-A tail-containing messenger RNAs (mRNAs).

When a synthetic strand of the present disclosure further comprises a series of solid supports each comprising on its surface a moiety for binding to A, C, G, or T/U, where each solid support of the series binds exclusively to A, C, G, or T/U, the series may be provided at any desirable location of the synthetic strand. In some embodiments, a synthetic strand of the present disclosure comprises such a series at a terminus of the synthetic strand.

According to some embodiments, a synthetic strand of the present disclosure comprises such a series at each terminus of the synthetic strand. In certain embodiments, a synthetic strand of the present disclosure comprises one or more such series internal to the synthetic strand.

According to some embodiments, when a synthetic strand of the present disclosure further comprises a series of solid supports each comprising on its surface a moiety for binding to A, C, G, or T/U, where each solid support of the series binds exclusively to A, C, G, or T/U, one or more (e.g., each) of the solid supports of the series are not rotatable (e.g., fixed in a position/orientation that enables the moiety to bind the nucleobase of the corresponding nucleotide of the nucleic acid without rotating). In certain embodiments, when a synthetic strand of the present disclosure further comprises a series of solid supports each comprising on its surface a moiety for binding to A, C, G, or T/U, where each solid support of the series binds exclusively to A, C, G, or T/U, one or more (e.g., each) of the solid supports of the series are rotatable.

The synthetic strands of the present disclosure may include any desired number of solid supports. The plurality of rotatable solid supports may comprise a number of solid supports sufficient to obtain the sequence of a nucleic acid molecule of interest or portion thereof. In certain embodiments, the plurality of rotatable solid supports comprises from 10 to 10,000 solid supports. For example, the plurality of rotatable solid supports may comprise from 10 to 7500, 10 to 5000, 10 to 2500, 10 to 2000, 10 to 1000, 10 to 900, 10 to 800, 10 to 700, 10 to 600, 10 to 500, 10 to 400, 10 to 300, 10 to 200, 10 to 150, or 10 to 100 rotatable solid supports. In certain embodiments, the synthetic strand comprises 10,000 or fewer, but 10 or more, 50 or more, 75 or more, 100 or more, 200 or more, 300 or more, 400 or more, 500 or more, 600 or more, 700 or more, 800 or more, 900 or more, 1000 or more, 200 or more, 2500 or more, 5000 or more, or 7500 or more rotatable solid supports. According to some embodiments, the synthetic strand comprises 10 or more, but 1000 or fewer, 900 or fewer, 800 or fewer, 700 or fewer, 600 or fewer, 500 or fewer, 400 or fewer, 300 or fewer, 200 or fewer, 100 or fewer, or 50 or fewer rotatable solid supports.

According to some embodiments, the synthetic strand comprises one or more solid supports that are magnetic. For example, one or both of the terminal solid supports of a synthetic strand of the present disclosure may be magnetic. In certain embodiments, two or more solid supports at one or both ends of a synthetic strand of the present disclosure are magnetic. A solid support of a synthetic strand may be magnetic, e.g., by virtue of comprising one or more paramagnetic and/or superparamagnetic substances, such as for example, magnetite. Such paramagnetic and/or superparamagnetic substances may be embedded within the matrix of the solid supports, and/or may be disposed on an external and/or internal surface of the solid support. Including one or more magnetic solid supports at one or more regions (e.g., one or both termini) of the synthetic strands may be desirable for a variety of reasons, including but not limited to, enabling the separation of the synthetic strands (optionally present as nucleic acid-synthetic strand hybrid) from other components in a liquid medium, immobilizing one or both ends of the synthetic strands (optionally present as nucleic acid-synthetic strand hybrids) to one or more substrates to which the ends of the synthetic strands are magnetically attracted, and the like.

According to some embodiments, magnetically responsive solid supports are employed in order to facilitate a desired spacing between the solid supports. In certain embodiments, magnetically responsive solid supports are employed to increase the spacing of the solid supports (e.g., by altering the magnetic environment of the synthetic strand) relative to their spacing when hybridized to a nucleic acid, e.g., to facilitate reading of the position markers (e.g., to sequence the nucleic acid) subsequent to denaturing the synthetic strand from the nucleic acid.

In certain embodiments, the synthetic strands of the present disclosure further comprise solid support spacer moieties disposed along the one or more base strands between solid supports of the plurality of solid supports. In certain embodiments, the solid support spacer moieties are particulate in nature and may be made of any suitable materials including, but not limited to, organic or inorganic polymers, natural and synthetic polymers, including, but not limited to, agarose, cellulose, nitrocellulose, cellulose acetate, other cellulose derivatives, dextran, dextran-derivatives and dextran co-polymers, other polysaccharides, glass, silica gels, gelatin, polyvinyl pyrrolidone, rayon, nylon, polyethylene, polypropylene, polybutylene, polycarbonate, polyesters, polyamides, vinyl polymers, polyvinylalcohols, polystyrene and polystyrene copolymers, polystyrene cross-linked with divinylbenzene or the like, acrylic resins, acrylates and acrylic acids, acrylamides, polyacrylamides, polyacrylamide blends, co-polymers of vinyl and acrylamide, methacrylates, methacrylate derivatives and co-polymers, other polymers and co-polymers with various functional groups, latex, butyl rubber and other synthetic rubbers, silicon, glass, paper, natural sponges, insoluble protein, surfactants, metals, metalloids, magnetic materials, and any combinations thereof.

The positions of the solid support spacer moieties along the one or more base strands, the size of the solid support spacer moieties, or both, are adjustable to achieve a desired spacing between the solid supports. For example, according to some embodiments, the solid support spacer moieties are adapted to increase the spacing between the solid supports subsequent to denaturing the synthetic strand from a nucleic acid. Increasing the spacing between the solid supports in this context finds use, e.g., to facilitate reading of the position markers (e.g., to sequence the nucleic acid) subsequent to denaturing the synthetic strand from the nucleic acid.

The positions of the solid support spacer moieties along the one or more base strands, the size of the solid support spacer moieties, or both, may be adjustable by a variety of approaches. In some embodiments, the positions and/or size of the spacer moieties is responsive to a change in the environment of the of the synthetic strand. Such environmental changes may include, but are not limited to, temperature changes, chemical changes (e.g., pH changes), changes in the magnetic environment of the synthetic strand, and/or the like. Accordingly, in certain embodiments, the solid support spacer moieties comprise a material such that their positions are adjustable by altering the chemical environment of the synthetic strand. Also by way of example, the solid support spacer moieties may be magnetically responsive such that their positions are adjustable by altering the magnetic environment of the synthetic strand, a non-limiting example of which is exposing the synthetic strand to one or more magnetic fields.

In certain embodiments, one or more of the solid supports of the synthetic strand comprises a binding member. Non-limiting examples of binding members include biotin, desthiobiotin, avidin, streptavidin, an aptamer (see, e.g., Wilson & Szostak (1999) *Annu Rev Biochem.* 68:611-647), an MS2 coat protein-interacting sequence, a U1A protein-interacting sequence, etc. According to some embodiments, one or both of the terminal solid supports of a synthetic strand of the present disclosure comprise a binding member. In certain embodiments, two or more solid supports at one or both ends of a synthetic strand of the present disclosure comprise a binding member. Including one or more binding members at one or more regions (e.g., one or both termini) of the synthetic strands may be desirable for a variety of reasons, including but not limited to, immobilizing one or both ends of the synthetic strands (optionally present as nucleic acid-synthetic strand hybrids) to one or more substrates comprising the other binding member of the binding member pair. For example, a substrate (e.g., planar or non-planar substrate) may be functionalized with streptavidin, and immobilization of one or more synthetic strands to the substrate may be achieved by providing one or more biotinylated solid supports at an end of the one or more synthetic strands.

Also provided are substrates (e.g., planar and non-planar substrates) that comprise one or more (e.g., a plurality of) synthetic strands of the present disclosure (optionally present as nucleic acid-synthetic strand hybrids) immobilized on the surface thereof. The immobilization of a synthetic strand on the surface of the substrate may arise from one or more covalent bonds between the synthetic strand (e.g., an end thereof) and the surface of the substrate, one or more non-covalent bonds between the synthetic strand (e.g., an end thereof) and the surface of the substrate (e.g., an ionic or metallic bond), or other forms of chemical attraction, such as hydrogen bonding, Van der Waals forces, and the like. To aid in stabilizing the synthetic strands on the substrate, solid supports adjacent to the point of immobilization may be absent. The surface of the substrate may also be functionalized to include a chemical handle that reacts with a corresponding chemical handle on the synthetic strand to covalently immobilize the one or more synthetic strands (e.g., via their ends) on the surface of the substrate. For example, surface of the substrate may be functionalized with any useful/convenient reactive group, including but not limited to thiol groups (—SH), amine groups (—NH2), carboxyl groups (—COO), and/or the like.

When a plurality of synthetic strands are immobilized on the surface of a substrate, the plurality may include any desired number of synthetic strands limited by the surface area of the substrate. In some embodiments, provided is a substrate that comprises from 2 to 1 trillion synthetic strands, e.g., from 2 to 1 billion, from 2 to 750 million, from 2 to 500 million, from 2 to 250 million, from 2 to 1 million, from 2 to 750,000, from 2 to 500,000, from 2 to 250,000, from 2 to 100,000, from 2 to 75,000, from 2 to 50,000, from 2 to 25,000, from 2 to 10,000, from 2 to 7500, from 2 to 5000, from 2 to 2500, from 2 to 1000, from 2 to 750, from 2 to 500, from 2 to 250, from 2 to 100, from 2 to 75, from 2 to 50, from 2 to 25, from 2 to 10, or from 2 to 5 synthetic strands immobilized on the surface of the substrate.

In certain embodiments, an end of a synthetic strand of the present disclosure is immobilized to a surface of a first substrate, and the other end of the synthetic strand is immobilized to a surface of a second substrate. According to some embodiments, the distance between the surfaces of the first and second substrates is selected to provide a desired tension in the synthetic strand, e.g., to "pull" the synthetic strand into a substantially linear configuration. The desired tension may be, e.g., a tension that elongates the synthetic strand but retains the rotatable nature of the solid supports and the ability of the solid support to hybridize to a nucleic acid. As described elsewhere herein, suitable immobilization strategies include non-covalent (e.g., magnetic attraction, biotin-streptavidin attraction, or the like), covalent (e.g., by reacting compatible reactive groups), or any other convenient immobilization strategies.

Methods

Aspects of the present disclosure further include methods of using the synthetic strands of the present disclosure. In certain embodiments, provided are methods of sequencing a nucleic acid, where the methods comprise contacting a nucleic acid (e.g., in a test sample (e.g., blood, bone marrow, FFPE or isolated nucleic acids)) with a synthetic strand of the present disclosure under conditions in which rotatable solid supports of the synthetic strand hybridize to nucleotides of the nucleic acid to produce a synthetic strand-nucleic acid hybrid. On such hybridization, rotation of the solid support ceases. Methods are further providing to determine the rotational positions of the solid supports of the synthetic strand-nucleic acid hybrid, and determine a nucleotide sequence of the nucleic acid based on the determined rotational positions of the solid supports.

The contacting of the nucleotide moieties of a synthetic strand with a nucleic acid of interest is performed under conditions in which rotatable solid supports of the synthetic strand specifically hybridize to a region of the nucleic acid. Conditions for specific hybridization may be determined by such factors as the temperature at which the hybridization occurs, which may be informed by the melting temperature (T M) of the nucleic acid. The melting temperature refers to the temperature at which half of the synthetic strand-nucleic acid duplexes remain hybridized and half of the duplexes dissociate into single strands. The Tm of a duplex may be experimentally determined or predicted using the following formula Tm=81.5+16.6(log 10[Na+])+0.41 (fraction G+C)−(60/N), where N is the chain length and [Na+] is less than 1 M. See Sambrook and Russell (2001; Molecular Cloning: A Laboratory Manual, 3rd ed., Cold Spring Harbor Press, Cold Spring Harbor N.Y., Ch. 10). Other more advanced models that depend on various parameters may also be used to predict Tm of synthetic strand-nucleic acid duplexes depending on various hybridization conditions. Approaches for achieving specific nucleic acid hybridization may be found in, e.g., Tijssen, Laboratory Techniques in Biochemistry and Molecular Biology-Hybridization with Nucleic Acid Probes, part I, chapter 2, "Overview of principles of hybridization and the strategy of nucleic acid probe assays," Elsevier (1993).

According to some embodiments, the contacting is performed under conditions in which the strength of binding of the rotatable solid supports to A or T is substantially equivalent to the strength of binding of the rotatable solid supports to C or G. For example, the pH of the liquid medium in which the contacting occurs may be selected to achieve equivalent strength of binding between A-T and C-G. Guidance regarding selecting a suitable pH may be found, e.g., in Brown et al. (1990) J. Mol. Biol. 212:437-440; Ageno et al. (1969) Biophysical Journal 9:1281-1311; and elsewhere. In some embodiments, the selected pH is in a range of from pH 7.5 to 11.5, e.g., 7.5 to 8.5, 8.5 to 9.5, 9.5 to 10.5, or 10.5 to 11.5.

Figure 1:
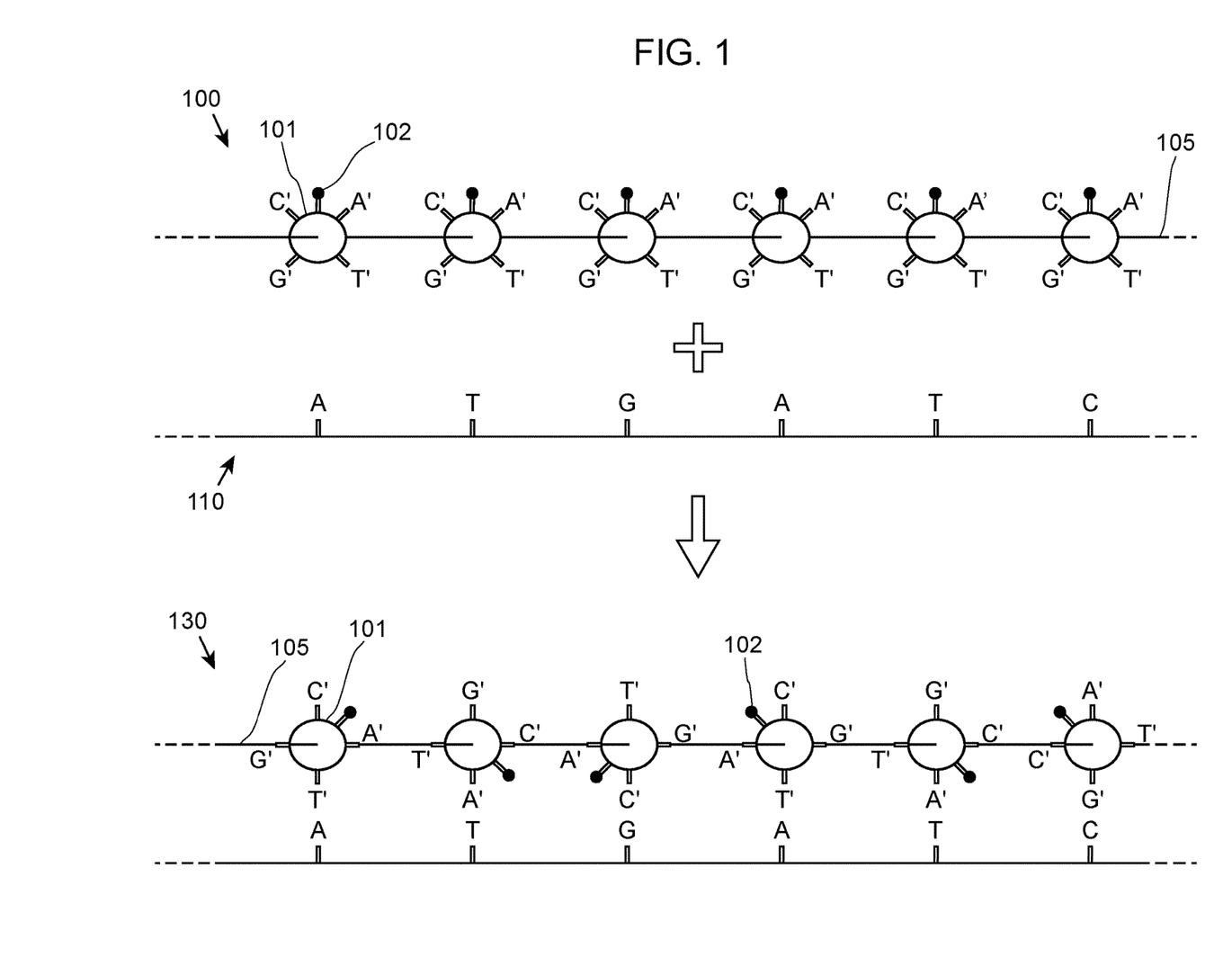
FIG. 1 Hybridization between a synthetic strand and a nucleic acid via base pairing creates a duplex in which relative orientation of the position markers are fixed.

FIG. 1 depicts an exemplary embodiment of the subject methods. A synthetic strand 100 is contacted with nucleic acid 110 under hybridization condition to produce duplex 130 by base pairing between the nucleotides of the nucleic acid and the nucleotides or nucleotide analogs present on rotatable solid supports 101. In this particular embodiment, position marker 102 is located between A' and T' on the rotatable solid supports. Prior to hybridization, rotatable solid supports 101 freely rotate about base strand 105. Upon hybridization to a nucleic acid, the position of position marker 102 on each of the rotatable solid supports 101 is fixed in the synthetic strand:nucleic acid duplex 130.

In certain embodiments, the methods further comprise, subsequent to producing the synthetic strand-nucleic acid hybrid and prior to determining the rotational positions of the solid supports, fixing the rotational positions of the solid supports. The rotational positions (e.g., post-hybridization rotational positions) of the solid supports may be fixed, e.g., by treating the synthetic strand of the synthetic strand-nucleic acid hybrid with a suitable agent. Suitable agents include fixatives, cross-linking agents, etc. Fixing the rotational positions of the solid supports prior to determining the rotational positions of the solid supports may be performed to ensure that the rotational positions of the solid supports accurately reflect the nucleotide sequence of the nucleic acid to which they hybridized.

In some embodiments, the rotational positions of the solid supports are fixed by crosslinking neighboring solid supports and/or surface components of neighboring solid supports, e.g., prior to denaturing the synthetic strand from the nucleic acid to which it is hybridized.

In certain embodiments, the methods of the present disclosure comprise denaturing the synthetic strand-nucleic acid hybrid prior to determining the rotational positions of the solid supports. According to some such embodiments, the methods further comprise, subsequent to the denaturing and prior to determining the rotational positions of the solid supports, increasing the spacing between the solid supports. Increasing the spacing between the solid supports in this context finds use, e.g., to facilitate reading of the position markers (e.g., to sequence the nucleic acid) subsequent to denaturing the synthetic strand from the nucleic acid. For example, the accuracy of determining the rotational positions of the solid supports may be enhanced when the separation between adjacent solid supports (and in turn their respective position markers) is increased relative to their separation when hybridized to the nucleic acid to be sequenced.

The spacing between solid supports may be increased by a variety of approaches. According to some embodiments, the spacing between the solid supports is increased by altering the environment of the synthetic strand. For example, the spacing between the solid supports may be increased by altering a parameter of the environment of the synthetic strand selected from temperature, chemical environment, magnetic environment, and any combination thereof. In certain embodiments, the solid supports are responsive to the alteration of the environment of the synthetic strand. In one non-limiting example, the solid supports may be magnetically responsive and the spacing between the solid supports is increased by altering the magnetic environment of the synthetic strand, e.g., exposing the synthetic strand to one or more magnetic fields. Alternatively, or additionally, the synthetic strand may comprise solid support spacer moieties disposed along the one or more base strands between solid supports of the plurality of solid supports, where the spacing between the solid supports is increased by increasing the spacing between the solid support spacer moieties, the size of the solid support spacer moieties, or both. According to some embodiments, the spacing between the solid support spacer moieties, the size of the solid support spacer moieties, or both, is increased by altering a parameter of the environment of the synthetic strand selected from temperature, chemical environment, magnetic environment, and any combination thereof. For example, the solid support spacer moieties may comprise a material that expands upon an increase in temperature, and the size of the solid support spacer moieties is increased (thereby increasing the spacing between the solid supports) by increasing the temperature of the environment of the synthetic strand. Also by way of example, the solid support spacer moieties may be magnetically responsive, and the spacing between the solid support spacer moieties (and in turn, the solid supports) is increased by altering the magnetic environment of the synthetic strand. In certain embodiments, altering the magnetic environment of the synthetic strand comprises exposing the synthetic strand to one or more magnetic fields. For example, a magnet or combination of two or more magnets may be placed in in sufficient proximity to the synthetic strand such that the magnetically responsive solid support spacer moieties increase their distance from one another, e.g., by repulsion or any other convenient mechanism.

The manner in which the rotational positions of the solid supports are determined may vary, and the manner may depend upon the type(s) of position markers employed. In certain embodiments, determining the rotational positions of the solid supports comprises reading the position markers in a sequential manner. According to some embodiments, the position markers are read in a sequential manner by translocating the synthetic strand (present in the synthetic strand-nucleic acid duplex, or fixed but dissociated from the nucleic acid to which it was hybridized) past a detection region, e.g., a fluorescence detection region (e.g., a photometer) when the position markers are fluorophores, a magnetic detection region when the position markers comprise magnetic molecules, or the like. Suitable detection regions include, but are not limited to, detection regions at or near a pore (e.g., a nanopore) through which the synthetic strand (present in the synthetic strand-nucleic acid duplex, or fixed but dissociated from the nucleic acid to which it was hybridized) is translocated. In certain embodiments, the synthetic strand is immobilized on a surface (e.g., as described above) and the position markers are read in a sequential manner by scanning the position markers of the immobilized synthetic strand in a sequential manner. According to some embodiments, two or more position markers are determined simultaneously, e.g., by capturing an image of two or more fluorophore-based position markers of the synthetic strand (present in the synthetic strand-nucleic acid duplex, or fixed but dissociated from the nucleic acid to which it was hybridized).

In certain embodiments, determining the rotational positions of the solid supports comprises reading the position markers in a sequential manner. According to some embodiments, the position markers emit a detectable signal, and reading the position markers in a sequential manner comprises detecting emissions from the position markers in a sequential manner. The detecting may comprise determining the direction of emissions from the position markers. For example, each of the solid supports may comprise one or more position markers at the same location on the solid support with respect to the moieties disposed thereon for binding to A, C, G, and T/U (e.g., disposed between C' and A' in the non-limiting example shown in FIG. 2), such that the direction of emissions from the position markers indicates the rotational positions of the solids supports, and in turn, the bases of the nucleic acid to which they are bound. In certain embodiments, determining the direction of emissions from the position markers is performed using a single detector, e.g., a stationary detector or a detector which is movable between two or more positions (e.g., "sides") relative to the synthetic strand. According to some embodiments, determining the direction of emissions from the position markers is performed using two or more detectors, e.g., a first detector positioned on a first side of the synthetic strand and a second detector positioned on a second side of the synthetic strand, e.g. to facilitate determining the direction of emissions from the positions markers. A non-limiting example of such a configuration is schematically illustrated in FIG. 2.

Figure 2:
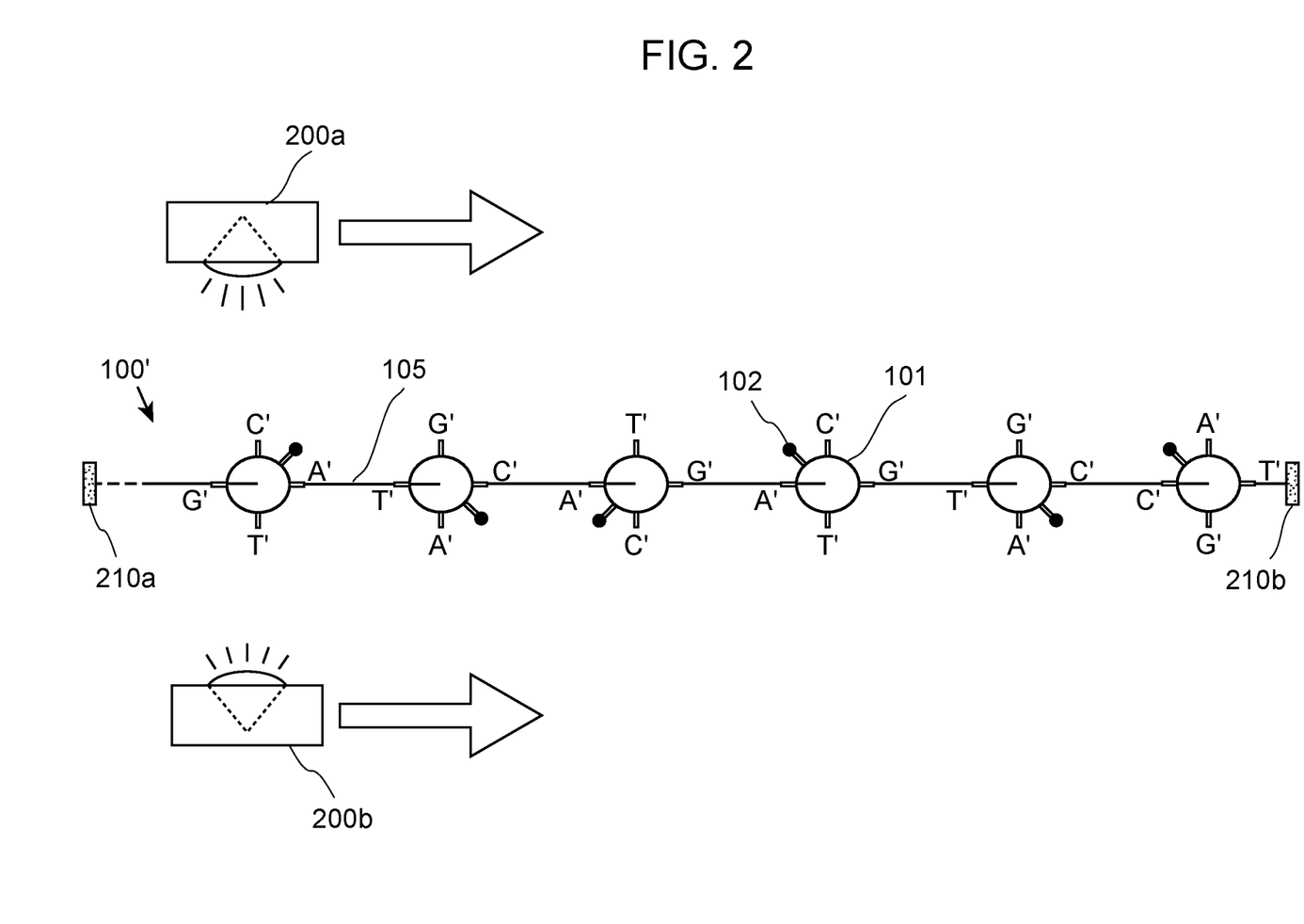
FIG. 2 The synthetic strand depicted in FIG. 1 is fixed to maintain the relative orientation of the position markers in absence of the nucleic acid. The fixed synthetic strand is immobilized by attaching the free ends to substrates. In certain embodiments, the spacing between the individual rotatable solid supports is increased to facilitate scanning and resolution of the position markers by the depicted detectors.

FIG. 2 illustrates an example of a post-hybridization synthetic strand 100' in which the rotational positions of solid supports 101 are fixed and synthetic strand 100' is extended and immobilized by attachment to first substrate 210a and second substrate 210b. In this example, position markers 102 are read from at least two different orientations using detectors 200a and 200b which scan position markers 102 of fixed synthetic strand 100' sequentially to determine the rotational positions of the solid supports and, in turn, the order of bases of the nucleic acid to which the synthetic strand was hybridized. According to some embodiments, the spacing between solid supports 101 is increased post-hybridization in order to facilitate resolution of the position markers. Example approaches for increasing the spacing between the solid supports prior to determining the rotational positions thereof are described elsewhere herein.

Attachment of the ends of the synthetic strand to one or more substrates may be covalent or non-covalent. In certain embodiments, the attachment is via magnetic attraction, e.g., between one or more magnetically-responsive terminal solid supports at a first end of the synthetic strand and a first magnetic substrate, and between one or more magnetically-responsive terminal solid supports at the second end of the synthetic strand and a second magnetic substrate; between one or more biotinylated terminal solid supports at a first end of the synthetic strand and a first streptavidin functionalized substrate, and between one or more biotinylated terminal solid supports at the second end of the synthetic strand and a second streptavidin functionalized substrate; or the like.

According to some embodiments, the methods of the present disclosure are computer-implemented. By "computer-implemented" is meant at least one step of the method is implemented using one or more processors and one or more non-transitory computer-readable media. The computer-implemented methods of the present disclosure may further comprise one or more steps that are not computer-implemented, e.g., obtaining a sample from a subject, isolating nucleic acids for sequencing, and/or the like.

A nucleic acid to be sequenced according to the methods of the present disclosure may be a deoxyribonucleic acid (DNA). DNAs of interest include, but are not limited to, genomic DNA or fragments thereof, complementary DNA (or "cDNA", synthesized from any RNA or DNA of interest) or fragments thereof, recombinant DNA (e.g., plasmid DNA) or fragments thereof, and/or the like.

A nucleic acid to be sequenced according to the methods of the present disclosure may be a ribonucleic acid (RNA). The RNA may be any type of RNA (or sub-type thereof) including, but not limited to, a messenger RNA (mRNA), a microRNA (miRNA), a small interfering RNA (siRNA), a transacting small interfering RNA (ta-siRNA), a natural small interfering RNA (nat-siRNA), a ribosomal RNA (rRNA), a transfer RNA (tRNA), a small nucleolar RNA (snoRNA), a small nuclear RNA (snRNA), a long non-coding RNA (lncRNA), a non-coding RNA (ncRNA), a transfer-messenger RNA (tmRNA), a precursor messenger RNA (pre-mRNA), a small Cajal body-specific RNA (scaRNA), a piwi-interacting RNA (piRNA), an endoribonuclease-prepared siRNA (esiRNA), a small temporal RNA (stRNA), a signal recognition RNA, a telomere RNA, a ribozyme, or any combination of RNA types thereof or subtypes thereof.

A nucleic acid to be sequenced according to the methods of the present disclosure may be a nucleic acid from one or more immune cells. Immune cells of interest include, but are not limited to, T cells, B cells, natural killer (NK) cells, macrophages, monocytes, neutrophils, dendritic cells, mast cells, basophils, and eosinophils. In certain embodiments, the nucleic acid to be sequenced is from a T cell. T cells of interest include naive T cells ($T_N$), cytotoxic T cells ($T_{CTL}$), memory T cells ($T_{MEM}$), T memory stem cells (Tacna), central memory T cells ($T_{CM}$), effector memory T cells ($T_{EM}$), tissue resident memory T cells ($T_{RM}$), effector T cells ($T_{EFF}$), regulatory T cells ($T_{REGS}$), helper T cells ($T_H$, $T_H1$, $T_H2$, $T_H17$) CD4+ T cells, CD8+ T cells, virus-specific T cells, alpha beta T cells ($T_{\alpha\beta}$), and gamma delta T cells ($T_{\gamma\delta}$).

In certain embodiments, a nucleic acid to be sequenced according to the methods of the present disclosure is a nucleic that encodes an immune cell receptor (e.g., a T cell receptor (TCR), a B cell receptor (BCR)) or a portion thereof. For example, in certain embodiments, provided are methods that comprise sequencing a nucleic acid that encodes one or more CDRs of an alpha chain or a beta chain of a TCR. According to some embodiments, the methods comprise sequencing a CDR3-encoding portion of a nucleic acid that encodes all or a portion of an alpha chain or a beta chain of a TCR. In certain embodiments, such methods employ a synthetic strand comprising a series of solid supports each comprising on its surface a moiety for binding to A, C, G, or T/U, where each solid support of the series binds exclusively to A, C, G, or T/U, and where the series is designed to hybridize to a known nucleotide sequence (e.g., a constant region sequence) adjacent the CDR3-encoding portion of the nucleic acid that encodes all or a portion of an alpha chain or a beta chain of a TCR, such that the nucleotide sequence of the CDR3-encoding portion may be determined based on the rotational positions of the solid supports adjacent the series of solid supports.

The nucleic acids to be sequenced according to the methods of the present disclosure may be present in any nucleic acid sample of interest. In certain embodiments, the nucleic acids are present in a nucleic acid sample isolated from a single cell, a plurality of cells (e.g., cultured cells), a tissue, an organ, or an organism (e.g., bacteria, yeast, or the like). According to some embodiments, the nucleic acid sample is isolated from a cell(s), tissue, organ, and/or the like of an animal. In some embodiments, the animal is a mammal, e.g., a mammal from the genus Homo (e.g., a human), a rodent (e.g., a mouse or rat), a dog, a cat, a horse, a cow, or any other mammal of interest. In certain embodiments, the nucleic acid sample is isolated/obtained from a source other than a mammal, such as bacteria, yeast, insects (e.g., *drosophila*), amphibians (e.g., frogs (e.g., *Xenopus*)), viruses, plants, or any other non-mammalian nucleic acid sample source.

Nucleic acids that may be sequenced according to the methods of the present disclosure include cell-free nucleic acids, e.g., cell-free DNA, cell-free RNA, or both. Such cell-free nucleic acids may be obtained from any suitable source. In certain embodiments, the cell-free nucleic acids are from a body fluid sample selected from the group consisting of: whole blood, blood plasma, blood serum, amniotic fluid, saliva, urine, pleural effusion, bronchial lavage, bronchial aspirates, breast milk, colostrum, tears, seminal fluid, peritoneal fluid, pleural effusion, and stool. In certain embodiments, the cell-free nucleic acids are cell-free fetal DNAs. According to some embodiments, the cell-free nucleic acids are circulating tumor DNAs. In certain embodiments, the cell-free nucleic acids comprise infectious agent DNAs. According to some embodiments, the cell-free nucleic acids comprise DNAs from a transplant.

The term "cell-free nucleic acid" as used herein can refer to nucleic acid isolated from a source having substantially no cells. Cell-free nucleic acid may be referred to as "extracellular" nucleic acid, "circulating cell-free" nucleic acid (e.g., CCF fragments, ccf DNA) and/or "cell-free circulating" nucleic acid. Cell-free nucleic acid can be present in and obtained from blood (e.g., from the blood of an animal, from the blood of a human subject). Cell-free nucleic acid often includes no detectable cells and may contain cellular elements or cellular remnants. Non-limiting examples of acellular sources for cell-free nucleic acid are described above. Obtaining cell-free nucleic acid may include obtaining a sample directly (e.g., collecting a sample, e.g., a test sample) or obtaining a sample from another who has collected a sample. According to some embodiments, a cell-free nucleic acid may be a product of cell apoptosis and cell breakdown, which provides basis for cell-free nucleic acid often having a series of lengths across a spectrum (e.g., a "ladder"). In some embodiments, sample nucleic acid from a test subject is circulating cell-free nucleic acid. In some embodiments, circulating cell free nucleic acid is from blood plasma or blood serum from a test subject.

Cell-free nucleic acid can include different nucleic acid species, and therefore is referred to herein as "heterogeneous" in certain embodiments. For example, a sample from a subject having cancer can include nucleic acid from cancer cells (e.g., tumor, neoplasia) and nucleic acid from non-cancer cells. In another example, a sample from a pregnant female can include maternal nucleic acid and fetal nucleic acid. In another example, a sample from a subject having an infection or infectious disease can include host nucleic acid and nucleic acid from the infectious agent (e.g., bacteria, fungus, protozoa). In another example, a sample from a subject having received a transplant can include host nucleic acid and nucleic acid from the donor organ or tissue. In some instances, cancer, fetal, infectious agent, or transplant nucleic acid sometimes is about 5% to about 50% of the overall nucleic acid (e.g., about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49% of the total nucleic acid is cancer, fetal, infectious agent, or transplant nucleic acid). In another example, heterogeneous cell-free nucleic acid may include nucleic acid from two or more subjects.

Nucleic acids that may be sequenced according to the methods of the present disclosure include tumor nucleic acids (e.g., present in a nucleic acid sample isolated from a tumor—e.g., a tumor biopsy sample). "Tumor", as used herein, refers to all neoplastic cell growth and proliferation, whether malignant or benign, and all pre-cancerous and cancerous cells and tissues. The terms "cancer" and "cancerous" refer to or describe the physiological condition in mammals that is typically characterized by unregulated cell growth/proliferation. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, prostate cancer, vulval cancer, thyroid cancer, hepatic carcinoma, various types of head and neck cancer, and the like.

Approaches, reagents and kits for isolating, purifying and/or concentrating DNA and RNA from sources of interest are known in the art and commercially available. For example, kits for isolating DNA from a source of interest include the DNeasy®, RNeasy®, QIAamp®, QIAprep® and QIAquick® nucleic acid isolation/purification kits by Qiagen, Inc. (Germantown, Md); the DNAzol®, ChargeSwitch®, Purelink®, GeneCatcher® nucleic acid isolation/purification kits by Life Technologies, Inc. (Carlsbad, CA); the NucleoMag®, NucleoSpin®, and NucleoBond® nucleic acid isolation/purification kits by Clontech Laboratories, Inc. (Mountain View, CA). In certain embodiments, the nucleic acid is isolated from a fixed biological sample, e.g., formalin-fixed, paraffin-embedded (FFPE) tissue. Genomic DNA from FFPE tissue may be isolated using commercially available kits—such as the AllPrepe DNA/RNA FFPE kit by Qiagen, Inc. (Germantown, Md), the RecoverAll® Total Nucleic Acid Isolation kit for FFPE by Life Technologies, Inc. (Carlsbad, CA), and the NucleoSpin® FFPE kits by Clontech Laboratories, Inc. (Mountain View, CA).

Nucleic acid sequences determined according to the methods of the present disclosure may be analyzed (e.g., assembled and/or the like) using available sequence analysis software.

Kits

Aspects of the present disclosure further include kits. In certain embodiments, the kits find use, e.g., in performing any of the methods of the present disclosure. According to some embodiments, a kit of the present disclosure includes a plurality of any of the synthetic strands of the present disclosure, including any of the synthetic strands having any of the features described elsewhere herein (such as strands bound to a microplate or flow cell). Where a substrate with attached synthetic strands is provided, it is preferably washable so hybridized nucleic acids may be removed from the strands after reading so that the strands are reusable (improving sequencing cost efficiency).

A kit of the present disclosure may include one or more reagents that find use in sequencing nucleic acids using the synthetic strands. For example, a kit of the present disclosure may include a solution (e.g., a hybridization buffer solution) having a pH, salt concentration, one or more components (e.g., chelating agents), and/or the like useful for providing suitable conditions for contacting a nucleic acid to be sequenced with a synthetic strand, e.g., conditions in which the rotatable solid supports of the synthetic strand specifically hybridize to the nucleotides of the nucleic acid to produce a synthetic strand-nucleic acid hybrid. In certain embodiments, a kit of the present disclosure includes a reagent suitable to fix the rotational positions of the solid supports subsequent to producing the synthetic strand-nucleic acid hybrid and prior to determining the rotational positions of the solid supports.

A kit of the present disclosure may further include instructions for performing any of the methods of the present disclosure, e.g., instructions for using the synthetic strands to sequence nucleic acids. The instructions may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., portable flash drive, DVD, CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, the means for obtaining the instructions is recorded on a suitable substrate.

A kit of the present invention may also include or otherwise encompass instrumentation for reading the relative position of markers along a synthetic strand after completion of a hybridization reaction, thereby providing a nucleic acid sequencing system. Such instrumentation may include plate readers for detecting reactions suited to the position markers provided on the synthetic strands.

Computer-Readable Media and Systems

Also provided by the present disclosure are computer-readable media and systems.

Aspects of the present disclosure further include nucleic acid sequencing systems. In certain embodiments, such systems comprise one or more position marker readers (e.g., one, two, or more position marker readers), one or more processors, and one or more computer-readable media comprising instructions stored thereon, which when executed by the one or more processors, cause the one or more processors to use the one or more position marker readers to determine the sequence of a nucleic acid by reading position markers of a synthetic strand of the present disclosure, e.g., according to any of the methods of the present disclosure described elsewhere herein. According to some embodiments, the instructions cause the one or more processors to determine the rotational positions of the solid supports when the synthetic strand is hybridized to the nucleic acid. In certain embodiments, the instructions cause the one or more processors to determine the rotational positions of the solid supports subsequent to the synthetic strand being denatured from the nucleic acid, e.g., a post-hybridization synthetic strand that is immobilized on one or more substrates, e.g., where a first end of the synthetic strand is immobilized on a first substrate and the second end of the synthetic strand is immobilized on a second substrate. A non-limiting example of such a configuration is shown in FIG. 2.

In certain embodiments, the instructions cause the one or more processors to read the position markers in a sequential manner, e.g., by detecting emissions from the position markers in a sequential manner. According to some embodiments, the instructions cause the one or more processors to read the position markers in a sequential manner by determining the direction of emissions from the position markers. For example, each of the solid supports may comprise one or more position markers at the same location on the solid support with respect to the moieties disposed thereon for binding to A, C, G, and T/U (e.g., disposed between C' and A' in the non-limiting example shown in FIG. 2), such that the direction of emissions from the position markers indicates the rotational positions of the solid supports, and in turn, the bases of the nucleic acid to which they are bound. As such, in certain embodiments, the instructions cause the one or more processors to determine the direction of emissions from the position markers (in turn determining the rotational positions of the solid supports), and determine a nucleotide sequence of the nucleic acid based on the determined rotational positions of the solid supports. The instructions may cause the one or more processors to scan/read the position markers using one or more detectors of the system—e.g., fluorescence detectors in the case of the position markers comprising fluorophores. As will be appreciated, the instructions may further cause the one or more processors—using one or more sources of suitable excitation radiation—to excite the fluorophores such that the position markers emit detectable fluorescence. A variety of suitable excitation sources and detectors for fluorescence detection are known and may be employed in the systems of the present disclosure, e.g., in one or more position marker readers of the systems of the present disclosure.

In certain embodiments, the instructions cause the one or more processors to determine the direction of emissions from the position markers using a single detector, e.g., a stationary detector or a detector which is movable between two or more positions (e.g., "sides") relative to the synthetic strand. According to some embodiments, the instructions cause the one or more processors to determine the direction of emissions from the position markers using two or more detectors, e.g., a first detector positioned on a first side of the synthetic strand and a second detector positioned on a second side of the synthetic strand, e.g. to facilitate determining the direction of emissions from the positions markers. A non-limiting example of such a configuration is schematically illustrated in FIG. 2.

A variety of processor-based systems may be employed to implement the embodiments of the present disclosure. Such systems may include system architecture wherein the components of the system are in electrical communication with each other using a bus. System architecture can include a processing unit (CPU or processor), as well as a cache, that are variously coupled to the system bus. The bus couples various system components including system memory, (e.g., read only memory (ROM) and random access memory (RAM), to the processor.

System architecture can include a cache of high-speed memory connected directly with, in close proximity to, or integrated as part of the processor. System architecture can copy data from the memory and/or the storage device to the cache for quick access by the processor. In this way, the cache can provide a performance boost that avoids processor delays while waiting for data. These and other modules can control or be configured to control the processor to perform various actions. Other system memory may be available for use as well. Memory can include multiple different types of memory with different performance characteristics. Processor can include any general purpose processor and a hardware module or software module, such as first, second and third modules stored in the storage device, configured to control the processor as well as a special-purpose processor where software instructions are incorporated into the actual processor design. The processor may essentially be a completely self-contained computing system, containing multiple cores or processors, a bus, memory controller, cache, etc. A multi-core processor may be symmetric or asymmetric.

To enable user interaction with the computing system architecture, an input device can represent any number of input mechanisms, such as a microphone for speech, a touch-sensitive screen for gesture or graphical input, keyboard, mouse, motion input, speech and so forth. An output device can also be one or more of a number of output mechanisms. In some instances, multimodal systems can enable a user to provide multiple types of input to communicate with the computing system architecture. A communications interface can generally govern and manage the user input and system output. There is no restriction on operating on any particular hardware arrangement and therefore the basic features here may easily be substituted for improved hardware or firmware arrangements as they are developed. The storage device is typically a non-volatile memory and can be a hard disk or other types of computer-readable media which can store data that are accessible by a computer, such as magnetic cassettes, flash memory cards, solid state memory devices, digital versatile disks, cartridges, random access memories (RAMs), read only memory (ROM), and hybrids thereof.

The storage device can include software modules for controlling the processor. Other hardware or software modules are contemplated. The storage device can be connected to the system bus. In one aspect, a hardware module that performs a particular function can include the software component stored in a computer-readable medium in connection with the necessary hardware components, such as the processor, bus, output device, and so forth, to carry out various functions of the disclosed technology.

Embodiments within the scope of the present disclosure may also include tangible and/or non-transitory computer-readable storage media or devices for carrying or having computer-executable instructions or data structures stored thereon. Such tangible computer-readable storage devices can be any available device that can be accessed by a general purpose or special purpose computer, including the functional design of any special purpose processor as described above. By way of example, and not limitation, such tangible computer-readable devices can include RAM, ROM, EEPROM, CD-ROM or other optical disk storage, magnetic disk storage or other magnetic storage devices, or any other device which can be used to carry or store desired program code in the form of computer-executable instructions, data structures, or processor chip design. When information or instructions are provided via a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable storage devices.

Computer-executable instructions include, for example, instructions and data which cause a general purpose computer, special purpose computer, or special purpose processing device to perform a certain function or group of functions. Computer-executable instructions also include program modules that are executed by computers in stand-alone or network environments. Generally, program modules include routines, programs, components, data structures, objects, and the functions inherent in the design of special-purpose processors, etc. that perform tasks or implement abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Other embodiments of the disclosure may be practiced in network computing environments with many types of computer system configurations, including personal computers, hand-held devices, multi-processor systems, microprocessor-based or programmable consumer electronics, network PCs, minicomputers, mainframe computers, and the like. Embodiments may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices.

In certain aspects, provided are one or more computer-readable media having stored thereon instructions for performing any of the steps of the methods of the present disclosure using any of the synthetic strands of the present disclosure. According to some embodiments, provided are the one or more computer-readable media of any of the systems of the present disclosure. For example, provided are one or more computer-readable media comprising instructions stored thereon, which when executed by one or more processors, cause the one or more processors to use one or more position marker readers to determine the sequence of a nucleic acid by reading position markers of a synthetic strand of the present disclosure during or subsequent to hybridization of the synthetic strand to the nucleic acid.

Notwithstanding the appended claims, the present disclosure is also defined by the following embodiments:

1. A synthetic strand for nucleic acid sequencing, comprising:
   a plurality of rotatable solid supports, wherein the plurality of rotatable solid supports comprises solid supports each comprising on its surface:
   a first moiety that binds to adenine (A);
   a second moiety that binds to cytosine (C);
   a third moiety that binds to guanine (G),
   a fourth moiety that binds to thymine (T), uracil (U), or both (T/U); and
   a position marker that indicates the rotational position of the solid support, wherein the first, second, third, and fourth moieties are spaced about the circumference of the solid support, and
   wherein the solid supports are sized and spaced along one or more base strands to enable hybridization of the synthetic strand to a nucleic acid.

2. The synthetic strand of embodiment 1, further comprising a series of solid supports each comprising on its surface a moiety for binding to A, C, G, or T/U, wherein each solid support of the series binds exclusively to A, C, G, or T/U, and wherein the series is designed to hybridize to a known nucleic acid sequence.

3. The synthetic strand of embodiment 2, wherein the known sequence is an adapter sequence.

4. The synthetic strand of embodiment 2 or embodiment 3, wherein the known sequence is a homopolymeric sequence.

5. The synthetic strand of embodiment 4, wherein the homopolymeric sequence is a polyA sequence.

6. The synthetic strand of embodiment 2, wherein the known sequence is a genomic DNA sequence.

7. The synthetic strand of embodiment 6, wherein the genomic DNA sequence is in a gene that encodes a T cell receptor or B cell receptor.

8. The synthetic strand of embodiment 2, wherein the known sequence is an mRNA sequence or a cDNA sequence.

9. The synthetic strand of embodiment 8, wherein the sequence is in an mRNA or cDNA that encodes a T cell receptor or B cell receptor.

10. The synthetic strand of any one of embodiments 2 to 9, wherein the series of solid supports is at a terminus of the synthetic strand.

11. The synthetic strand of any one of embodiments 2 to 9, wherein the series of solid supports is internal to the synthetic strand.

12. The synthetic strand of any one of embodiments 2 to 11, wherein the solid supports of the series are rotatable.

13. The synthetic strand of any one of embodiments 2 to 11, wherein the solid supports of the series are not rotatable.

14. The synthetic strand of any one of embodiments 1 to 13, wherein the solid supports are beads.
15. The synthetic strand of any one of embodiments 1 to 13, wherein the solid supports are cube-shaped or cuboidal.
16. The synthetic strand of any one of embodiments 1 to 15, comprising from 10 to 10,000 solid supports.
17. The synthetic strand of embodiment 16, comprising 1,000 or fewer solid supports.
18. The synthetic strand of embodiment 16, comprising 500 or fewer solid supports.
19. The synthetic strand of any one of embodiments 1 to 18, wherein one or more of the solid supports are magnetic.
20. The synthetic strand of embodiment 19, wherein a terminal solid support of the synthetic strand is magnetic.
21. The synthetic strand of embodiment 20, wherein the terminal solid supports of the synthetic strand are magnetic.
22. The synthetic strand of any one of embodiments 1 to 21, wherein one or more of the solid supports comprise a binding member.
23. The synthetic strand of embodiment 22, wherein the binding member comprises biotin.
24. The synthetic strand of any one of embodiments 1 to 23, further comprising solid support spacer moieties disposed along the one or more base strands between solid supports of the plurality of solid supports, wherein the positions of the solid support spacer moieties along the one or more base strands, the size of the solid support spacer moieties, or both, are adjustable to achieve a desired spacing between the solid supports.
25. The synthetic strand of embodiment 24, wherein the solid support spacer moieties are adapted such that their positions, size, or both, are adjustable by altering the environment of the synthetic strand.
26. The synthetic strand of embodiment 24, wherein the solid support spacer moieties comprise a material such that their positions are adjustable by altering a parameter of the environment of the synthetic strand selected from the group consisting of: temperature, chemical environment, magnetic environment, and any combination thereof.
27. The synthetic strand of embodiment 25 or embodiment 26, wherein the solid support spacer moieties comprise a material such that their positions, size, or both, are adjustable by altering the chemical environment of the synthetic strand.
28. The synthetic strand of any one of embodiments 24 to 27, wherein the solid support spacer moieties are magnetically responsive such that their positions are adjustable by exposing the solid support spacer moieties to one or more magnetic fields.
29. The synthetic strand of any one of embodiments 24 to 28, wherein the solid support spacer moieties are adapted to increase the spacing between the solid supports subsequent to denaturing the synthetic strand from a nucleic acid.
30. The synthetic strand of any one of embodiments 1 to 29, wherein the synthetic strand is immobilized on a surface.
31. The synthetic strand of embodiment 30, wherein an end of the synthetic strand is attached to the surface.
32. The synthetic strand of embodiment 30, wherein both ends of the synthetic strand are attached to the surface.
33. The synthetic strand of any one of embodiments 30 to 32, wherein the surface is the surface of a planar substrate.
34. The synthetic strand of any one of embodiments 30 to 32, wherein the surface is the surface of a non-planar substrate.
35. The synthetic strand of any one of embodiments 1 to 34, wherein the first, second, third, and fourth moieties comprise a nucleobase.
36. The synthetic strand of embodiment 35, wherein the nucleobase is a natural nucleobase.
37. The synthetic strand of embodiment 35, wherein the nucleobase is a non-natural nucleobase.
38. The synthetic strand of any one of embodiments 1 to 37, wherein the position markers of the plurality of rotatable solid supports are independently selected from the group consisting of: a fluorophore, a quencher, a magnetic molecule, and a metal.
39. The synthetic strand of any one of embodiments 1 to 37, wherein the position markers of the plurality of rotatable solid supports are fluorophores.
40. The synthetic strand of embodiment 38, wherein the position markers of the plurality of rotatable solid supports comprise fluorophore-quencher pairs.
41. The synthetic strand of any one of embodiments 1 to 40, wherein a first end of the synthetic strand is attached to a first substrate, and wherein the second end of the synthetic strand is attached to a second substrate.
42. A substrate having attached to the surface thereof the synthetic strand of any one of embodiments 1 to 40.
43. A substrate having attached to the surface thereof a plurality of synthetic strands of any one of embodiments 1 to 41.
44. A method of sequencing a nucleic acid, comprising:
    contacting the nucleic acid with the synthetic strand of any one of embodiments 1 to under conditions in which the rotatable solid supports hybridize to the nucleotides of the nucleic acid to produce a synthetic strand-nucleic acid hybrid;
    using the position markers, determining the rotational positions of the solid supports; and
    determining a nucleotide sequence of the nucleic acid based on the determined rotational positions of the solid supports.
45. The method according to embodiment 44, wherein the conditions comprise conditions under which the strength of binding of the rotatable solid supports to A or T is substantially equivalent to the strength of binding of the rotatable solid supports to C or G.
46. The method according to embodiment 44 or embodiment 45, further comprising, subsequent to producing the synthetic strand-nucleic acid hybrid and prior to determining the rotational positions of the solid supports, fixing the rotational positions of the solid supports.
47. The method according to any one of embodiments 44 to 46, wherein the rotational positions of the solid supports are determined when the synthetic strand is hybridized to the nucleic acid.
48. The method according to embodiment 44 or embodiment 45, further comprising, subsequent to producing the synthetic strand-nucleic acid hybrid and prior to determining the rotational positions of the solid supports, fixing the rotational positions of the solid supports and denaturing the synthetic strand-nucleic acid hybrid, wherein the rotational positions of the solid supports are determined subsequent to denaturing the synthetic strand-nucleic acid hybrid.
49. The method according to embodiment 48, wherein subsequent to denaturing the synthetic strand-nucleic acid hybrid and prior to determining the rotational positions of the solid supports, the synthetic strand is immobilized on a substrate.
50. The method according to embodiment 49, wherein a first end of the synthetic strand is covalently or non-covalently attached to the substrate.
51. The method according to embodiment 50, wherein the second end of the synthetic strand is covalently or non-covalently attached to the same or a different substrate.
52. The method according to any one of embodiments 48 to 51, further comprising, subsequent to denaturing the synthetic strand-nucleic acid hybrid and prior to determining the rotational positions of the solid supports, increasing the spacing between the solid supports.
53. The method according to embodiment 52, wherein increasing the spacing between the solid supports comprises altering the environment of the synthetic strand.
54. The method according to embodiment 53, wherein the spacing between the solid supports is increased by altering a parameter of the environment of the synthetic strand selected from the group consisting of: temperature, chemical environment, magnetic environment, and any combination thereof.
55. The method according to any one of embodiments 52 to 54, wherein the solid supports are magnetically responsive, and wherein the spacing between the solid supports is increased by altering the magnetic environment of the synthetic strand.
56. The method according to embodiment 55, wherein the magnetic environment of the synthetic strand is altered by exposing the synthetic strand to one or more magnetic fields.
57. The method according to any one of embodiments 52 to 56, wherein the synthetic strand comprises solid support spacer moieties disposed along the one or more base strands between solid supports of the plurality of solid supports, and wherein the spacing between the solid supports is increased by increasing the spacing between the solid support spacer moieties.
58. The method according to embodiment 57, wherein the spacing between the solid support spacer moieties is increased by altering the environment of the synthetic strand.
59. The method according to embodiment 57 or embodiment 58, wherein the spacing between the solid support spacer moieties is increased by altering a parameter of the environment of the synthetic strand selected from the group consisting of: temperature, chemical environment, magnetic environment, and any combination thereof.
60. The method according to any one of embodiments 57 to 59, wherein the solid support spacer moieties are magnetically responsive, and wherein the spacing between the solid support spacer moieties is increased by altering the magnetic environment of the synthetic strand.
61. The method according to embodiment 60, wherein the magnetic environment of the synthetic strand is altered by exposing the synthetic strand to one or more magnetic fields.
62. The method according to any one of embodiment 44 to 61, wherein determining the rotational positions of the solid supports comprises reading the position markers in a sequential manner.
63. The method according to embodiment 62, wherein the position markers emit a detectable signal, and wherein reading the position markers in a sequential manner comprises detecting emissions from the position markers in a sequential manner.
64. The method according to embodiment 63, wherein the detecting comprises determining the direction of emissions from the position markers.
65. The method according to embodiment 63 or embodiment 64, wherein the detecting is performed using a single detector.
66. The method according to embodiment 63 or embodiment 64, wherein the detecting is performed using two or more detectors.
67. The method according to any one of embodiments 62 to 66, wherein the position markers are fluorophores, and wherein the reading the position markers in a sequential manner comprises detecting fluorescence emitted from the position markers in a sequential manner using one or more fluorescence emission detectors.
68. The method according to any one of embodiments 44 to 67, wherein the nucleic acid is a genomic DNA.
69. The method according to embodiment 68, wherein the genomic DNA comprises all or a portion of a gene that encodes a chain of a T cell receptor or a B cell receptor.
70. The method according to any one of embodiments 44 to 67, wherein the nucleic acid is an mRNA.
71. The method according to any one of embodiments 44 to 67, wherein the nucleic acid is a cDNA.
72. The method according to embodiment 70 or embodiment 71, wherein the nucleic acid encodes all or a portion of a chain of a T cell receptor or a B cell receptor.
73. A nucleic acid sequencing system, comprising:
a position marker reader;
one or more processors; and
one or more computer-readable media comprising instructions stored thereon, which when executed by the one or more processors, cause the one or more processors to use the position marker reader to determine the sequence of a nucleic acid by reading position markers of the synthetic strand of any one of embodiments 1 to 40 during or subsequent to hybridization of the synthetic strand to the nucleic acid.
74. The nucleic acid sequencing system of embodiment 73, wherein the instructions cause the system to perform the method of any one of embodiments 44 to 72.
75. One or more computer-readable media having stored thereon instructions for performing the method of any one of embodiments 44 to 72.
76. A kit, comprising:
a plurality of synthetic strands of any one of embodiments 1 to 40; and
instructions for using the synthetic strands to sequence nucleic acids.

Accordingly, the preceding merely illustrates the principles of the present disclosure. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein.

What is claimed is:

1. A method of sequencing a nucleic acid, comprising:
contacting the nucleic acid with a synthetic strand comprising a plurality of rotatable solid supports, wherein the plurality of rotatable solid supports comprises solid supports each comprising on its surface:
a first moiety that binds to adenine (A);
a second moiety that binds to cytosine (C);
a third moiety that binds to guanine (G);
a fourth moiety that binds to thymine (T), uracil (U), or both (T/U); and
a position marker that indicates the rotational position of the solid support, wherein the first, second, third, and fourth moieties are spaced about the circumference of the solid support,
wherein the solid supports are sized and spaced along one or more base strands to enable hybridization of the synthetic strand to the nucleic acid, and
wherein the contacting is under conditions in which the rotatable solid supports hybridize to the nucleotides of the nucleic acid to produce a synthetic strand-nucleic acid hybrid;
determining the rotational positions of the solid supports by reading the position markers in a sequential manner, wherein the position markers emit a detectable signal, and wherein reading the position markers in a sequential manner comprises detecting emissions from the position markers in a sequential manner; and
determining a nucleotide sequence of the nucleic acid based on the determined rotational positions of the solid supports.

2. The method according to claim 1, further comprising, subsequent to producing the synthetic strand-nucleic acid hybrid and prior to determining the rotational positions of the solid supports, fixing the rotational positions of the solid supports.

3. The method according to claim 1, wherein the rotational positions of the solid supports are determined when the synthetic strand is hybridized to the nucleic acid.

4. The method according to claim 1, further comprising, subsequent to producing the synthetic strand-nucleic acid hybrid and prior to determining the rotational positions of the solid supports, fixing the rotational positions of the solid supports and denaturing the synthetic strand-nucleic acid hybrid, wherein the rotational positions of the solid supports are determined subsequent to denaturing the synthetic strand-nucleic acid hybrid.

5. The method according to claim 1, wherein the detecting comprises determining the direction of emissions from the position markers.

6. The method according to claim 5, wherein the detecting is performed using a single detector.

7. The method according to claim 5, wherein the detecting is performed using two or more detectors.

8. The method according to claim 1, wherein the nucleic acid is a genomic DNA.

9. The method according to claim 1, wherein the nucleic acid is an mRNA.

10. A nucleic acid sequencing system, comprising:
one or more position marker readers;
one or more processors; and
one or more computer-readable media comprising instructions stored thereon, which when executed by the one or more processors, cause the one or more processors to use the one or more position marker readers to determine the sequence of a nucleic acid according to the method of claim 1 during or subsequent to hybridization of the synthetic strand to the nucleic acid.

11. The nucleic acid sequencing system of claim 10, wherein the nucleic acid sequencing system is adapted to fix the rotational positions of the solid supports subsequent to hybridization of the synthetic strand to the nucleic acid and prior to determining the rotational positions of the solid supports.

12. The nucleic acid sequencing system of claim 10, wherein the nucleic acid sequencing system is adapted to increase the spacing between the solid supports prior to determining the rotational positions of the solid supports.

13. The nucleic acid sequencing system of claim 12, wherein the nucleic acid sequencing system is adapted to increase the spacing between the solid supports by altering a parameter of the environment of the synthetic strand selected from the group consisting of: temperature, chemical environment, magnetic environment, and any combination thereof.

14. The nucleic acid sequencing system of claim 13, wherein the solid supports are magnetically responsive, and wherein the spacing between the solid supports is increased by altering the magnetic environment of the synthetic strand.

15. The nucleic acid sequencing system of claim 10, wherein the one or more position marker readers are adapted to determine the direction of emissions from the position markers.

16. The nucleic acid sequencing system of claim 15, comprising a single position marker reader adapted to determine the direction of emissions from the position markers.

17. The nucleic acid sequencing system of claim 15, comprising two or more position marker readers adapted to determine the direction of emissions from the position markers.

18. The nucleic acid sequencing system of claim 10, wherein the position markers are fluorophores, and wherein the one or more position marker readers comprise one or more fluorescence emission detectors.

19. A kit, comprising:
a plurality of synthetic strands, each synthetic strand comprising a plurality of rotatable beads, wherein the plurality of rotatable beads comprises beads each comprising on its surface:
a first moiety that binds to adenine (A);
a second moiety that binds to cytosine (C);
a third moiety that binds to guanine (G);
a fourth moiety that binds to thymine (T), uracil (U), or both (T/U); and
a position marker that indicates the rotational position of the bead, wherein the first, second, third, and fourth moieties are spaced about the circumference of the bead, wherein the beads are sized and spaced along one or more base strands to enable hybridization of the synthetic strand to the nucleic acid; and instructions for using the synthetic strands to sequence nucleic acids.

20. The kit of claim 19, wherein the plurality of synthetic strands comprise a series of solid supports each comprising on its surface a moiety for binding to A, C, G, or T/U, wherein each solid support of the series binds exclusively to A, C, G, or T/U, and wherein the series is designed to hybridize to a known nucleic acid sequence.

\* \* \* \* \*